(12) United States Patent
Lang et al.

(10) Patent No.: US 7,381,221 B2
(45) Date of Patent: Jun. 3, 2008

(54) MULTI-ZONAL MONOFOCAL INTRAOCULAR LENS FOR CORRECTING OPTICAL ABERRATIONS

(75) Inventors: Alan J. Lang, Long Beach, CA (US); Huawei Zhao, Irvine, CA (US)

(73) Assignee: Advanced Medical Optics, Inc., Santa Ana, CA (US)

(*) Notice: Subject to any disclaimer, the term of this patent is extended or adjusted under 35 U.S.C. 154(b) by 0 days.

(21) Appl. No.: 10/705,548

(22) Filed: Nov. 10, 2003

(65) Prior Publication Data

US 2004/0106992 A1 Jun. 3, 2004

Related U.S. Application Data

(60) Provisional application No. 60/424,851, filed on Nov. 8, 2002.

(51) Int. Cl.
*A61F 2/16* (2006.01)
(52) U.S. Cl. ..................... 623/6.24; 623/6.28
(58) Field of Classification Search ....... 623/6.23–6.33
See application file for complete search history.

(56) References Cited

U.S. PATENT DOCUMENTS

| | | |
|---|---|---|
| 4,504,982 A | 3/1985 | Burk |
| 4,564,484 A | 1/1986 | Neefe |
| 4,906,246 A | 3/1990 | Grendahl |
| 5,050,981 A | 9/1991 | Roffman |
| 5,112,351 A | 5/1992 | Christie et al. |
| 5,158,572 A | 10/1992 | Nielsen |
| 5,181,053 A | 1/1993 | Brown |
| 5,191,366 A | 3/1993 | Kashiwagi |
| 5,220,359 A | 6/1993 | Roffman |
| 5,270,744 A | 12/1993 | Portney et al. |
| 5,589,024 A | 12/1996 | Blake |
| 5,684,560 A | 11/1997 | Roffman et al. |
| 5,777,719 A | 7/1998 | William et al. |
| 6,007,747 A | 12/1999 | Blake et al. |
| 6,024,447 A | 2/2000 | Portney |
| 6,082,856 A | 7/2000 | Dunn et al. |

(Continued)

FOREIGN PATENT DOCUMENTS

EP   0 742 466 A   11/1996

(Continued)

OTHER PUBLICATIONS

Prospective Randomized Trial of an Anterior Surface Modified Prolate Intraocular Lens, *Journal of Refractive Surgery*, vol. 18, Nov./Dec. 2002, pp. 692-696.

*Primary Examiner*—Paul B. Prebilic
*Assistant Examiner*—David A. Izquierdo
(74) *Attorney, Agent, or Firm*—Advanced Medical Optics, Inc.

(57) ABSTRACT

A multi-zonal monofocal opthalmic lens comprises an inner zone, an intermediate zone, and an outer zone. The inner zone has a first optical power. The intermediate zone surrounds the inner zone and has a second optical power that is different from the first power by a magnitude that is less than at least about 0.75 Diopter. The outer zone surrounds the intermediate zone and has a third optical power different from the second optical power. In certain embodiments, the third optical power is equal to the first optical power.

3 Claims, 5 Drawing Sheets

U.S. PATENT DOCUMENTS

| | | |
|---|---|---|
| 6,126,286 A | 10/2000 | Portney |
| 6,224,211 B1 | 5/2001 | Gordon |
| 6,338,559 B1 | 1/2002 | William et al. |
| 6,454,408 B1 | 9/2002 | Morris et al. |
| 6,474,814 B1 | 11/2002 | Griffin |
| 6,596,025 B2 | 7/2003 | Portney |
| 6,609,793 B2 | 8/2003 | Norrby et al. |
| 6,638,305 B2 | 10/2003 | Laguette |
| 6,663,240 B2 | 12/2003 | Patel |
| 6,705,729 B2 | 3/2004 | Piers et al. |
| 6,764,179 B2 | 7/2004 | Sakai |
| 6,797,003 B1 | 9/2004 | Blake et al. |
| 7,018,409 B2 * | 3/2006 | Glick et al. ............... 623/6.24 |
| 2002/0063848 A1 | 5/2002 | Fiala |
| 2003/0199976 A1 | 10/2003 | Portney |
| 2004/0054408 A1 | 3/2004 | Glick et al. |
| 2004/0230299 A1 | 11/2004 | Simpson et al. |
| 2004/0246440 A1 | 12/2004 | Andino et al. |

FOREIGN PATENT DOCUMENTS

| | | |
|---|---|---|
| EP | 0900403 B1 | 3/1999 |
| WO | WO92/22000 A1 | 12/1992 |
| WO | WO 01/89424 A1 | 11/2001 |
| WO | WO02/074210 A2 | 9/2002 |
| WO | WO2004/089252 A2 | 10/2004 |

\* cited by examiner

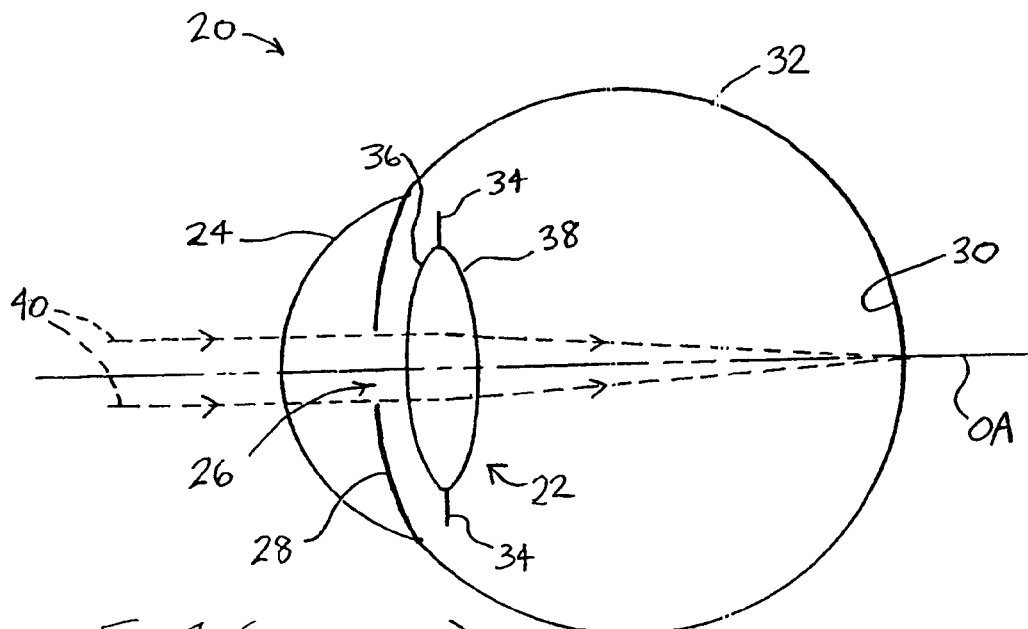
Fig. 1 (BRIGHT LIGHT)
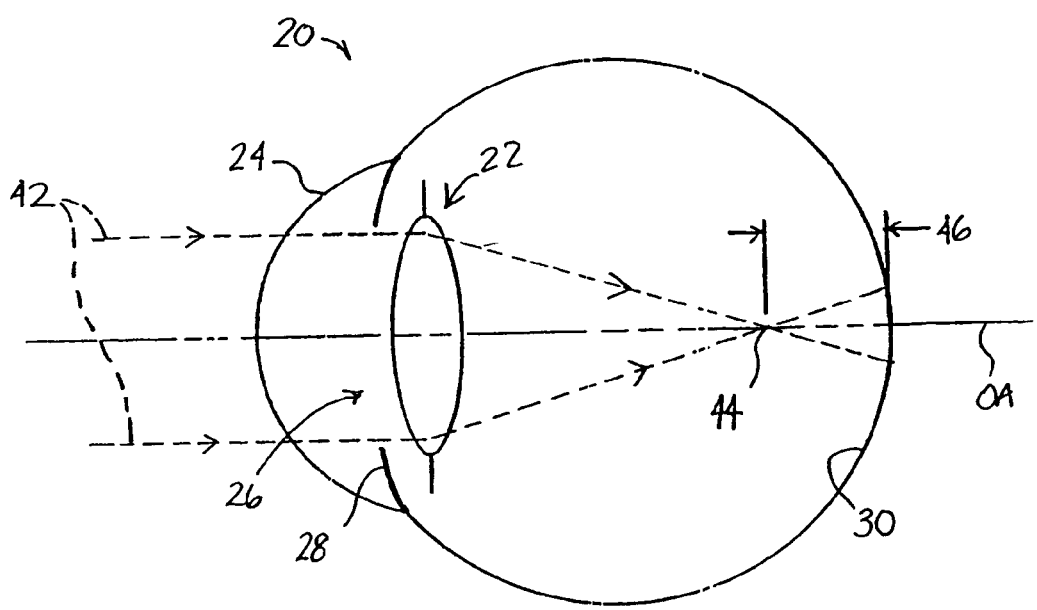
Fig. 2 (LOW LIGHT)

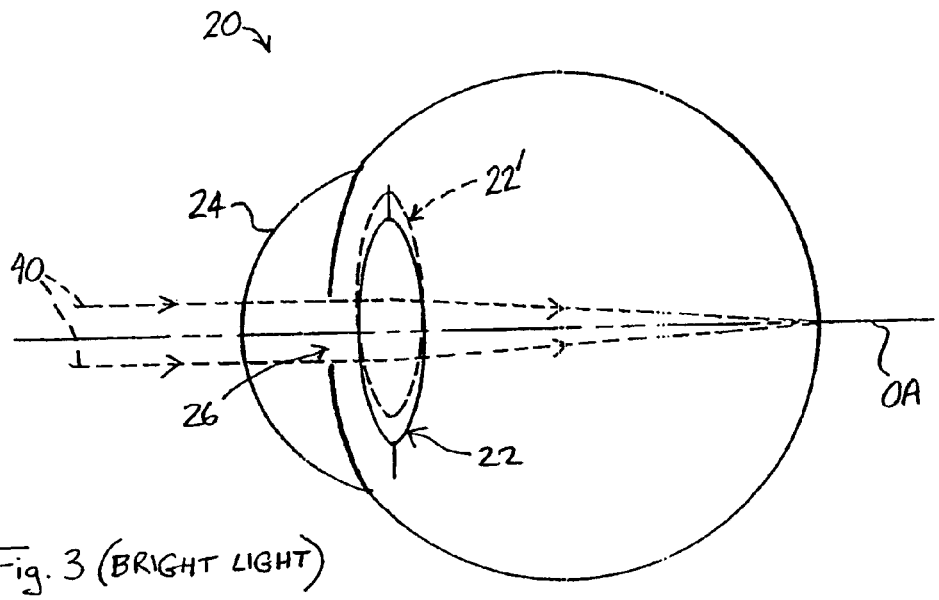
Fig. 3 (BRIGHT LIGHT)
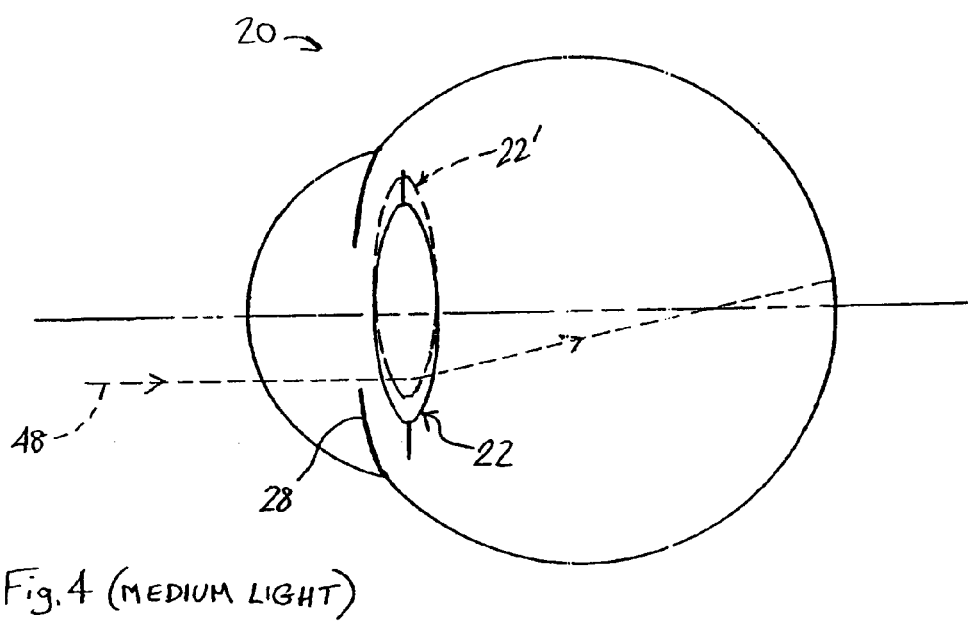
Fig. 4 (MEDIUM LIGHT)

MULTI-ZONAL MONOFOCAL INTRAOCULAR LENS FOR CORRECTING OPTICAL ABERRATIONS

RELATED APPLICATION

The present application claims priority under 35 U.S.C §119(e) to provisional application No. 60/424,851, filed on Nov. 8, 2002 under the same title. Full Paris Convention priority is hereby expressly reserved.

FIELD OF THE INVENTION

This invention relates to intraocular lenses (IOLs) and, more particularly, to multi-zonal monofocal IOLs that correct optical aberrations for a variety of human eyes with different corneas under a wide range of lighting conditions and that are effective even when decentered or tilted.

BACKGROUND OF THE INVENTION

In the perfect eye, an incoming beam of light is focused through the cornea and through the crystalline lens in a way that causes all of the light from a point source to converge at the same spot on the retina of the eye, ideally on the fovea area of the retina. This convergence occurs because all of the optical path lengths, for all light in the beam, are equal to each other. Stated differently, in the perfect eye the time for all light to transit through the eye will be the same regardless of the particular path that is taken by the light.

Not all eyes, however, are perfect. The consequences of this are that light path lengths through the eye become distorted and are not all equal to each other. Thus, light from a point source that transits an imperfect eye will not necessarily come to the same spot on the retina and be focused.

As light enters and passes through an eye it is refracted at the anterior surface of the cornea, at the posterior surface of the cornea, and at the anterior and posterior surfaces of the crystalline lens, finally reaching the retina. Any deviations that result in unequal changes in these optical path lengths are indicative of imperfections in the eye that may need to be corrected. For example, many people are near-sighted because the axial length of their eyes are "too long" (myopia). As a result, the sharp image of an object is generated not on the retina, but in front of or before the retina. Hyperopia is a condition where the error of refraction causes rays of light to be brought to a focus behind the retina. This happens because the axial length is "too short". This condition is commonly referred to as farsightedness. Another refractive malady is astigmatism resulting from a refractive surface with unequal curvatures in two meridians. The different curvatures cause different refractive powers, spreading light in front and in back of the retina.

Other "higher order" maladies of interest for vision correction include coma and spherical aberration. Coma exists when an asymmetry in the optical system causes unequal optical path lengths in a preferred direction. For example, the image of an off-axis point object takes on a comet-like shape. For symmetrical systems, spherical aberration exists when rays at different radial heights from the optical axis focus at different axial locations near the retina. Whereas coma exists only in asymmetric systems, spherical aberration can exist in both symmetric and asymmetric systems. Other, even higher order, aberrations exist. However, studies have show that spherical aberration is one of the strongest higher order aberrations in the human visual system. Thus the retinal image may be improved if the spherical aberration is corrected according to known techniques.

Studies have also shown that there is a balance between the positive spherical aberration of the cornea and the negative spherical aberration of the crystalline lens in younger eyes. As one grows older, the spherical aberration of the crystalline lens becomes more positive, increasing the overall spherical aberration and reducing the image quality at the retina.

An intraocular lens (IOL) is commonly used to replace the natural lens of a human eye when warranted by medical conditions such as cataracts. In cataract surgery, the surgeon removes the natural crystalline lens from the capsular bag or posterior capsule and replaces it with an IOL. IOLs may also be implanted in an eye (e.g., in the anterior chamber) with no cataract to supplement the refractive power of the natural crystalline lens, correcting large refractive errors.

The majority of ophthalmic lenses including IOLs are monofocal, or fixed focal length, lenses that primarily correct refractive error. Most monofocal IOLs are designed with spherical anterior and posterior surfaces. The spherical surfaces of the typically positive power IOLs cause positive spherical aberration, inter alia. Thus, replacement of the crystalline lens with a typical monofocal IOL leaves the eye with positive spherical aberration. In real eyes with complex corneal aberrations, the eye following cataract surgery is left a with finite number of complex lower and higher order aberrations, limiting the image quality on the retina.

Some examples of attempts to measure higher order aberrations of the eye as an optical system in order to design an optical lens include U.S. Pat. No. 5,062,702 to Bille, et al., U.S. Pat. No. 5,050,981 to Roffman, U.S. Pat. No. 5,777,719 to Williams, et al., and U.S. Pat. No. 6,224,211 to Gordon.

A typical approach for improving the vision of a patient has been to first obtain measurements of the eye that relate to the topography of the anterior surface of the cornea. Specifically, the topography measurements yield a mathematical description of the anterior surface of the cornea. This corneal surface is placed in a theoretical model of the patient's eye with an IOL replacing the crystalline lens. Ray-tracing techniques are employed to find the IOL design which corrects for the spherical aberration of the cornea. Ideally, if implanted with this custom IOL, the patient's vision will improve.

Recently, Pharmacia Corp. (Groningen, Netherlands) introduced a posterior capsule intraocular lens having the trade name TECNIS (Z9000) brand of Silicone IOL. The TECNIS lens has a prolate anterior surface, which is intended to reduce spherical aberrations of the cornea. This lens may be designed using methods described in U.S. Pat. No. 6,609,793 and PCT publication WO 01/89424, both to Norrby, et al. The methods in these publications involve characterizing aberrant corneal surfaces as linear combinations of Zernike polynomials, and then modeling or selecting an intraocular lens which, in combination with a characteristic corneal surface, reduces the optical aberrations ocular system. The lenses resulting from these methods may be continuous aspherical surfaces across the entire optical zone and may be used to reduce spherical aberrations of the eye by introducing negative spherical aberration to counter the typically positive spherical aberration of the cornea. In these lenses, there may be a single base curve on which the aspheric surface is superimposed. As reported by J. T. Holliday, et al., "A New Intraocular Lens Designed to Reduce Spherical Aberration of Pseudophakic Eyes," Journal of Refractive Surgery 2002, 18:683-691, the Technics IOL has been found to be to improve visual contrast sensitivity at a frequency up to 18 cycles/degree.

The TECNIS brand of lens generally requires precise positioning in the capsular bag to provide improved optical quality over a spherical IOL (c.f., "Prospective Randomized Trial of an Anterior Surface Modified Prolate Intraocular Lens," Journal of Refractive sugery, Vo. 18, Nov/Dec 2002). Slight errors in decentration (radial translation) or tilt (axial rotation) greatly reduces the effectiveness of the lens, especially in low-light conditions, thus making the task of the surgeon more difficult. Furthermore, shrinkage of the capsular bag or other post-implantation anatomical changes can affect the alignment or tilt of the lens along the eye's optical axis. It is believed that the "typical" magnitude of decentration resulting from the implantation of an intraocular lens in an average case, and factoring in post-implantation movement, is less than about 1.0 mm, and usually less than about 0.5 mm. Most doctors agree that decentration of an IOL greater than about 0.15 to approximately 0.4 mm is clinically relevant (i.e., noticeably affects the performance of the optical system, according to those skilled in the art). Similarly, the "typical" magnitude of tilt resulting from the implantation of an intraocular lens in an average case, and factoring in post-implantation movement, is less than about 10 degrees, and usually less than about 5 degrees. Therefore, in practice, the benefits of the TECNIS brand of lens may be offset by its apparent drawbacks in the real world.

In view of the above, there remains a need for an intraocular lens that corrects for spherical aberrations in a variety of lighting conditions and is less sensitive to non-optimal states such as decentration and tilt of the IOL.

SUMMARY OF THE INVENTION

The present invention provides a multi-zonal monofocal ophthalmic lens that is less sensitive to its disposition in the eye by reducing aberrations, including the spherical aberration, over a range of decentration. The monofocal ophthalmic lenses of the present invention may also be configured to perform well across eyes with different corneal aberrations (e.g., different asphericities).

In one aspect of the invention, a multi-zonal monofocal opthalmic lens comprises an inner zone, an intermediate zone, and an outer zone. The inner zone has a first optical power. The intermediate zone surrounds the inner zone and has a second optical power that is different from the first power by a magnitude that is less than at least about 0.75 Diopter. The outer zone surrounds the intermediate zone and has a third optical power different from the second optical power. In certain embodiments, the third optical power is equal to the first optical power. The ophthalmic lens may comprise between 3 and 7 total zones, but favorably comprises between 3 and 5 total zones. However, ophthalmic lenses with more than seven total zones are consistent with embodiments of the invention.

In another aspect of the invention, a multi-zonal monofocal intraocular lens has an optic with a plurality of concentric optical zones centered on the optical axis. The zones are adapted to focus incoming light rays to form the image from one object. The intraocular lens optic includes an inner zone overlapping the optical axis of the lens that provides an image when the intraocular lens is centered on the optical axis of the human eye. A first surrounding zone concentric about the inner zone is adapted to compensate for optical aberrations resulting from implanted intraocular lens decentration of greater than at least about 0.1 mm.

The first surrounding zone may be configured to compensate for optical aberrations resulting from implanted intraocular lens decentration of greater than at least about 0.1 mm. The first surrounding zone may also compensate for optical aberrations resulting from implanted intraocular lens tilt of greater than at least about 1 degree. The power of the first surrounding zone preferably differs from the power of the inner zone by a magnitude that is less than or equal to at least about 0.75 Diopter. In an exemplary embodiment, the inner zone comprises a spherical surface and the first surrounding zone comprises an aspherical surface.

Another aspect of the invention includes a method of designing multi-zonal monofocal opthalmic lens. The method comprises providing an optical model of the human eye. The method further comprises an optical model of a lens comprising an inner zone, an intermediate zone, an outer zone, and zonal design parameters. The method also comprises adjusting the zonal design parameters based on an image output parameter for one or more non-optimal states of the lens.

The method may further include testing the intraocular lens over a wide range of clinically relevant corneal surface variations and dispositions of optical elements in the eye's optical system using ray-trace analysis techniques. Furthermore, the method may be repeated to modify zonal parameters and achieve a better average optical performance. Examples of conditions of asymmetry that the lens will correct include decentration, tilt, and corneal aberrations.

The invention, together with additional features and advantages thereof, may best be understood by reference to the following description taken in connection with the accompanying illustrative drawings in which like parts bear like reference numerals.

BRIEF DESCRIPTION OF THE DRAWINGS

FIG. 1 is a schematic vertical cross-section of the human eye in a bright light environment and showing a pair of light rays passing through the optical system of the cornea and an implanted intraocular lens of the prior art to focus on the retina.

FIG. 2 is a schematic vertical cross-section of the human eye in a low light environment and showing a pair of light rays passing through the optical system of the cornea and the peripheral regions of an implanted intraocular lens of the prior art to focus in front of the retina.

FIG. 3 is a schematic vertical cross-section of the human eye in a bright light environment and showing a pair of light rays passing through the optical system of the cornea and a decentered implanted intraocular lens of the prior art to focus on the retina.

FIG. 4 is a schematic vertical cross-section of the human eye in a medium light environment and showing a pair of light rays passing through the optical system of the cornea and a decentered implanted intraocular lens of the prior art to focus in front of the retina.

DETAILED DESCRIPTION

Figure 5A:
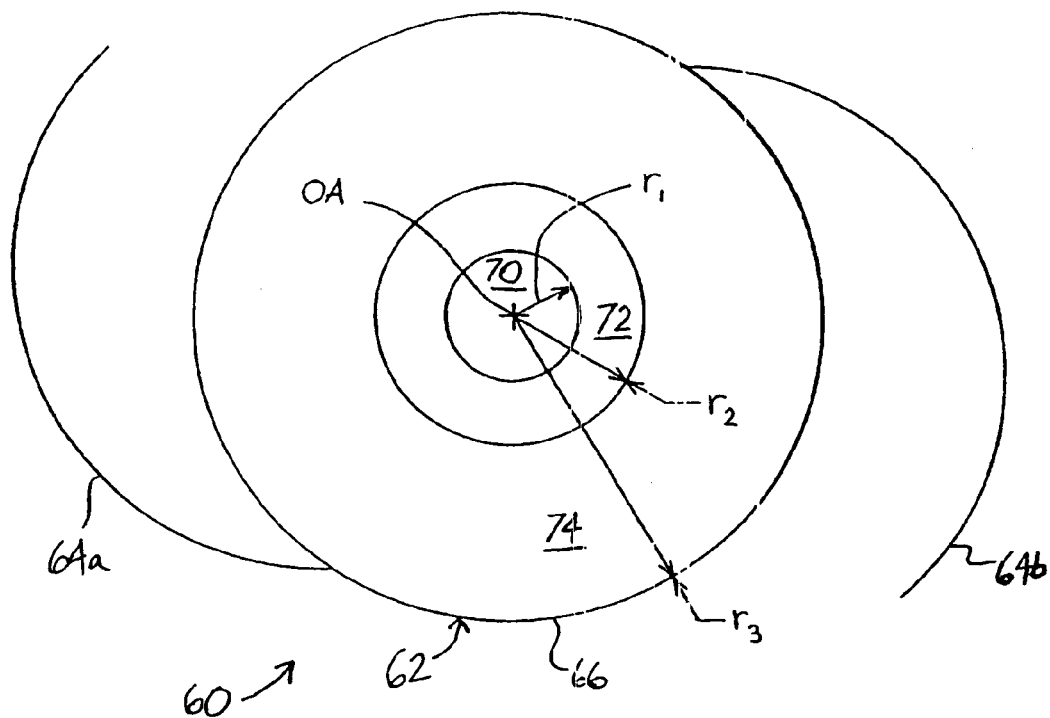
FIGS. 5A and 5B are schematic plan and side views of a monofocal intraocular lens of the present invention illustrating concentric zones about an optical axis.

The present invention encompasses an intraocular lens (IOL) design that reduces sensitivity to decentration within the eye while maintaining superior Module Transfer Function (MTF) performance for large pupils. The MTF is a measure of visual performance that can be plotted on a non-dimensional scale from a minimum of 0.0 to a maximum of 1.0 across a range of spatial frequencies in units of cycles per mm. The MTF is a measure of the efficiency of "transferring" the contrast of an object into an image. The spatial frequency is inversely proportional to the size of the object. Thus, small objects at the limit of visual resolution have high spatial frequencies than larger objects. The IOL described herein comprises a multi-zonal monofocal lens in which the anterior lens surface, posterior lens surface, or both comprises a plurality of zones that operate together on an incident wavefront to produce a corrected ocular image. The different zones of the IOL of the present invention, as described in greater detail below herein, generally have different mean spherical curvatures and/or Diopter powers, but the Diopter power differences between zones are far less than the typical 2 Diopter to 4 Diopter design differences associated with multi-focal IOLs. In certain embodiments, the maximum Diopter power difference between any two zones is less than at least about 0.75 D, advantageously less than about 0.65 D.

As used herein, the term "monofocal lens" is considered to be a lens in which light entering the lens from a distant point source is focused to substantially a single point. In the case of a multi-zonal monofocal lens, light from a distant point source entering the lens zones substantially fall within the range of the depth-of-focus of a spherical lens having an equivalent focal length.

As used herein in reference to the zones of a multi-zonal monofocal lens, the terms "optical power" and "Diopter power" refer to the effective optical or Diopter power of a zone when the lens is part of an ocular lens system such as, for example, a cornea, a multi-zonal monofocal IOL, a retina, and the material surrounding these components. This definition may include the effects of the vergence or angle of light rays intersecting the IOL surface caused by the power of the cornea. This may include the total vergence from all optical surfaces in front of the multi-zonal monofocal IOL. In certain instances, an algorithm for calculating the Diopter power may begin with a ray-tracing a model of the human eye incorporating a multi-zonal monofocal IOL. At a particular radial location on the IOL surface, Snell's law may be applied to calculate the angle of the light ray following the refraction. The optical path length of the distance between a point on the surface and the optical axis (axis of symmetry) may be used to define the local radius of curvature of the local wavefront. Using such an approach, the Diopter power is equal to the difference in indicies of refraction divided by this local radius of curvature.

IOLs of the present invention are designed to outperform certain IOLs of the prior art in low or moderate light situations over a larger range of implant positions. In practice, clinicians recognize that in the average case intraocular lenses implanted in the posterior capsule end up decentered from the optical axis of the host eye by between about 0.15-0.4 mm. Sometimes the decentration is greater as a result of poor implant technique or non-axisymmetric forces imparted by the host eye. Indeed, decentration of more than 0.5 mm, and sometimes up to 1.0 mm is experienced. IOLs of the present invention are specifically designed to exhibit superior performance in comparison to the prior art IOLs when decentered by at least about 0.15 mm and in particular in low or moderate light conditions. In certain embodiments, IOLs of the present invention are designed to exhibit superior performance in comparison to prior art IOLs when decentered by greater than about 0.5 mm or greater than about 1.0 mm. The amount of decentering to be accommodated depends upon design constraints such as, for example, the accuracy of the surgical method to be used for implanting the IOL. Since the multi-zonal monofocal IOLs provide improved performance for decentered conditions, it is anticipated that patients will generally experience greater satisfaction with a multi-zonal monofocal IOL than with other prior art IOLs.

FIG. 1 is a schematic vertical cross-section through a human eye 20 having an IOL 22 of the prior art implanted therein. The optical system of the eye 20 includes an outer cornea 24, a pupil 26 defined by an orifice of an iris 28, the IOL 22, and a retina 30 formed on the posterior inner surface of the ocular globe 32. In the present application, the terms anterior and posterior are used in their conventional sense; anterior refers to the front side of the eye closer to the cornea, while posterior refers to the rear side closer to the retina. The eye defines a natural optical axis OA. The drawing shows the eye 20 in a bright light environment with the iris 28 constricted resulting in a relatively small pupil 26.

The exemplary IOL 22 is adapted to be centered along the optical axis OA and within a capsular bag (not shown) just posterior to the iris 28. For this purpose, the IOL 22 may be provided with haptics or fixation members 34. An optic of the IOL 22 is defined by an anterior face 36 and posterior face 38. The optic may take a variety of configurations known in the art, such as the convex-convex configuration illustrated in FIG. 5B. It should be understood that the present invention is not limited to posterior capsule-implanted IOLs.

A pair of light rays 40 pass through cornea 24, pupil 26, the IOL 22. The rays 40 then focus on the retina 30 along the optical axis OA. In the bright light environment shown, the light rays 40 pass through the mid-portion of the lens optic. The intraocular lenses of the prior art are relatively effective in focusing such light rays at a point on the retina 30 along the optical axis OA.

FIG. 2 shows the eye 20 having the IOL 22 therein in a low light environment. In such situations, the iris 28 opens up creating a relatively large pupil 26 and permitting more light to strike the IOL 22. A pair of light rays 42 passing through the peripheral regions of the pupil 26 may be incorrectly refracted by the peripheral regions of the optic of the IOL 22 in the manner shown. That is, the light rays 42 focus on a spot 44 along the optical axis OA that is in front of the retina 30 by a distance 46. Such refraction is termed positive spherical aberration because the light rays 42 focus in front of the retina 30. A negative spherical aberration focuses light rays at the imaginary point along the optical axis OA behind the retina 30. Such aberrations can also occur in an eye with the natural lens still in place. For example, the crystalline lens in the aging eye may not refract light properly under low light environments. The practical result of such a condition may be a loss in image quality.

FIG. 3 illustrates the human eye 20 in a bright light environment such as shown in FIG. 1. The IOL 22 centered along the optical axis OA is again shown in solid line, but is also shown in dashed line 22' representing a condition of decentration. As mentioned above, decentration involves a radial translation of the intraocular lens from a centered configuration on the natural optical axis OA. The light rays 40 pass through the cornea 24 and relatively small pupil 26, and are refracted through the central region of the decentered intraocular lens optic 22'. That is, despite the undesirable decentration, the optic 22' performs well in bright light environments because light does not strike and refract through its peripheral regions.

FIG. 4 illustrates the eye 20 in a medium light environment, in which the iris 28 is somewhat larger compared to the condition shown in FIG. 3, but is not fully expanded as seen in the low light environment of FIG. 2. Under such conditions, a centered IOL 22 would likely perform adequately, but the decentered lens 22' will not. More particularly, a light ray 48 passing close to the iris 28 will strike and be incorrectly refracted through a peripheral region of the decentered optic 22' as shown. Intraocular lenses of the prior art have varying degrees of sensitivity to decentration, and the situation shown in FIG. 4 is for illustration purposes only and does not represent any particular lens.

However, it is believed that certain lenses designed to correct for spherical aberration, such as the TECNIS brand of lens, are relatively sensitive to small magnitudes of decentration. Such lenses have a complex refractive surface that changes relatively continuously across whichever face it is formed (i.e., anterior or posterior). This continuous refractive surface provides a negative correction for the positive spherical aberration on the cornea, but when the lens is decentered the closely calculated balance between the two optical devices may be lost. Indeed, other optical aberrations such as coma and astigmatism may be created by the resulting mismatch.

Figure 5B:
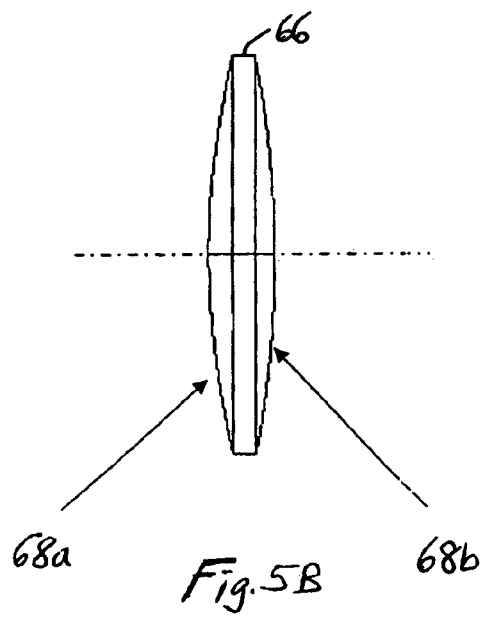

FIGS. 5A and 5B schematically illustrate in plan and side views a monofocal IOL 60 of the present invention having an optic 62 and a pair of haptics or fixation members 64a, 64b extending outward therefrom. The optic 62 has a generally circular peripheral edge 66 and a plurality of concentric annular refractive bands or zones formed thereon. The peripheral edge 66 is desirably an axially oriented edge with thickness, as seen in FIG. 5B, although curved or angled edge surfaces, or combinations thereof, are possible. The optic 62 has an anterior face 68a and an opposite posterior face 68b separated by the peripheral edge 66. It should be understood that the refractive zones can be formed on either the anterior or posterior face, or in some cases as a combination of both faces. A central and inner zone 70 centered on the optical axis OA extends outward to a radius of $r_1$, at least one intermediate zone 72 surrounds the inner zone 70 and extends outward to a radius of $r_2$, and an outer zone 74 surrounds the intermediate zone 72 and extends therefrom to the outer periphery 66 of the optic 62 and a radius of $r_3$. Desirably, $r_1$ is between about 1-1.5 mm, $r_2$ is between about 1.5-2.2 mm, and $r_3$ is about 3 mm. More desirably, $r_1$ is about 1.4 mm and $r_2$ is about 2.0 mm. certain instances, it may be desirable that $r_3$ is greater than 3 mm, for instance in order to preclude undesired edge effects.

The inner zone 70, intermediate zone 72, and outer zone 74 may have surfaces that are either spherical or aspherical in shape. The intermediate zone 72 may comprise a combination of annular zones, although a single annular zone is generally desirable. In certain embodiments, the inner zone 70 is spherical, the intermediate zone 72 is aspherical, and the outer zone 74 is also aspherical.

The power of the inner zone 70 dominates the visual performance of the eye when the pupil is small, such as in bright daylight situations. The intermediate zone 72 is at least designed to help correct aberrations of the IOL when it is decentered, tilted, or otherwise in a non-optimal state. The power of intermediate zone 72 is extremely close to that of the inner zone 70. The outer zone 74 may be aspherical and designed to minimize the spherical aberrations natural to spherical monofocal IOLs.

Preferably, the intermediate zone 72 has a correction power that is less than the correction power of the inner zone 70. When a prior art IOL is decentered (FIG. 4), peripheral light is too strongly refracted and focuses in front of the retina. However, the intermediate zone 72 of the multi-zonal monofocal IOL 60 is used to reduce surface power, redirecting the light ray 48 to the focal point on the retina. The intermediate zone 72 may also provide correction in cases of tilting of the lens within the typical range of at least about 1 to 10 degrees, depending upon design constraints such as, for example, the accuracy of the surgical method to be used for implanting the IOL.

The IOL 60 is considered to be a monofocal lens because the relative refractive powers of the zones 70, 72, and 74 are close to one another and within the range of the depth-of-focus of typical spherical monofocal IOLs. In this context, a "monofocal" lens is one in, which discrete adjacent regions or zones have a maximum difference in refractive power of less than at least about 0.75 Diopter. The refractive power of any one zone may be interpreted as the mean power within that zone. It should also be understood that discrete adjacent zones does not necessarily mean that there is a sharp physical transition therebetween, rather the manufacturing process may be designed to generally provide a smooth transition between adjacent zones.

The IOL 60 may be fabricated from materials used in the art, such as silicon, acrylic, or Polymethylmethacrylate (PMMA), or any other material that is suitable for use in or on a human eye. Materials may also be selected so as to provide a desired optical performance. For instance, the refractive index is known to vary with different materials and may, therefore, be used as a design parameter for attaining a desired optical performance or affect from the IOL 60.

The IOL 60 may also be used in conjunction with other optical devices such as diffractive optical elements (DOE). For example, the anterior lens surface of the IOL 60 may comprise a multi-zonal surface and the posterior lens surface may contain a DOE such as a diffractive grating, or visa versa. Alternatively, the multi-zonal surface itself may comprise a DOE such as a diffractive grating. The DOE may also be used, for example, to correct for chromatic aberrations or to improve the performance of the IOL 60 when displaced from the optimal position (e.g., centered and normal to the optical axis). In certain embodiments, the DOE is disposed over only a portion of the one of the IOL surfaces. For example, the DOE may be disposed over the intermediate zone 72 and used as an additional parameter for improving the performance of the IOL 60.

The IOL 60 may be designed to have a nominal optical power suited for the particular environment in which it is to be used. It is anticipated that the nominal optical power of the IOL 60 will generally be within a range of about −20 Diopters to at least about +35 Diopters. Desirably, the optical power of the IOL 60 is between about 10 Diopters to at least about 30 Diopter. In certain applications, the optical power of the IOL 60 is approximately 20 Diopters, which is a typical optical power for the natural crystalline lens in a human eye.

Under low light environments, such as night-time, the human eye has a larger pupil (about 4.5-6 mm in diameter) and hence has a large spherical aberration (SA) that blurs the image. Clinically, the large-pupil eye is reported to have a lower contrast sensitivity and sometimes lower visual acuity. The TECNIS brand of lens has been reported to perform better than spherical IOLs in low light environments as judged by visual contrast sensitivity and visual acuity. According to simulations, however, this aspherical design is sensitive to decentration. A fraction of a millimeter decentration of such IOLs from the optical axis may dramatically break the balance of SA between IOL and cornea, and thus seriously degrade the eye's vision.

The inventors have discovered that spherical aberration can be reduced for both on-design and off-design conditions by forming a lens surface to have a multi-zonal structure, with each zone having different surface parameters, for example, the base radius of curvature. In contrast with the prior art single continuous aspheric surface, such as the TECNIS brand of lens described above, the surface sag of the IOL 60 (i.e. multi-zonal surface contour) may be determined using an equation that changes across the lens. In accordance with an exemplary embodiment of the present invention, the surface sag at any radius from the optical axis for an ith zone is given by the following equation:

$$Sag = \frac{C_i * r^2}{1 + \sqrt{1 - (1 + K_i) * C_i^2 * r^2}} + \sum_{j=0}^{M} B_{i,j} * (r - r_i)^{2j} + \sum_{j=1}^{M} T_{i,j} * (r - r_{i-1})^{2j}$$

where $C_i$, $K_i$, and $r_i$ are the base radius of curvature, the asphericity constant, and the height of the ith zonal surface. Further, the Bjs and Tjs are optional boundary parameters that can be used to connect the zonal surfaces smoothly. The variable M is an integer that determines how smoothly one zone transitions to another. This work makes use of a published finite eye model to represent the "nominal" eye for IOL design (see, Liou H. L. and Brennan N. A., "Anatomically Accurate, Finite Model Eye for Optical Modeling, J Opt Soc Am A, 1997; 14:1684-1695).

For posterior chamber IOL design, the asphericity constant $K_1$ in the inner zone 70 (FIG. 5A) is preferably zero (i.e., the inner zone 70 comprises a spherical surface). The base radius of curvature $C_1$ in the inner zone 70 is considered to be the base surface power of the lens. There are preferably at least three zones (i≧3) to achieve enhanced performance for a 6 mm diameter pupil size. A preferred range of the number of zones is between at least about 3-7, more preferably between 3-5; however, larger numbers of zones may be used of particular design conditions. The parameters in the outlying zones can be optimally determined such that each zonal surface refracts more of the light rays in that particular zone to the focus set by the inner zone. This process can be achieved by the aid of a commercial optical ray tracing design software, such as ZEMAX optical design program from ZEMAX Development Corporation (4901 Morena Blvd. Suite 207, San Diego, Calif. 92117-7320).

In general, the base curves in at least two zones are different (preferably the inner and intermediate zones), though all zones may have different base curves. Desirably, the anterior surface has three zones, each having a different base radius of curvature. The posterior surface is a one zone spherical surface.

Table 1 provides an example of a multi-zonal monofocal IOL consistent with the present invention. The values of the parameters given below are for an IOL with an overall Diopter power of 20 having 3 zones (i=3) on the anterior surface and one zone on the posterior (i=1).

TABLE I

Surface parameters of a 20D multi-zonal structured IOL

| | Symbol | i = 1 | i = 2 | i = 3 |
|---|---|---|---|---|
| Anterior surface parameter | | | | |
| Zonal outer radial boundary, mm | $r_i$ (mm) | 1.414 | 2.000 | 3.000 |
| Zonal curvature of radius, 1/mm | $C_i$ (1/mm) | 0.08614900000 | 0.0751110000000 | 0.05055500000000 |
| Zonal asphericity | $K_i$ | 0.00000000000000 | −1.5931120000000 | 8.90504900000000 |
| M = 3 | $B_{i0}$ | 0.00163052185449 | 0.01542174622418 | 0.11151991935001 |
| | $B_{i1}$ | −0.0024465216312 | −0.0241315485668 | −0.0611825408097 |
| | $B_{i2}$ | 0.00122363035200 | 0.08421200000000 | 0.00963200000000 |
| | $B_{i3}$ | −0.0002040000000 | −0.1293190000000 | 0.00399800000000 |
| | $T_{i1}$ | 0.00000000000000 | .02774300000000 | −0.0571790000000 |
| | $T_{i2}$ | −0.0004750000000 | −0.1375720000000 | 0.13027200000000 |
| | $T_{i3}$ | 0.00007700000000 | 0.23032800000000 | −0.0800460000000 |
| Posterior surface parameter | | | | |
| Zonal outer radial boundary, mm | $r_i$ (mm) | 3.000 | | |
| Zonal curvature of radius, 1/mm | $C_i$ (1/mm) | 0.0636027120000 | | |
| Zonal asphericity | $K_i$ | 0.00000000000000 | | |
| M = 0 | N/A | | | |

Figure 6A:
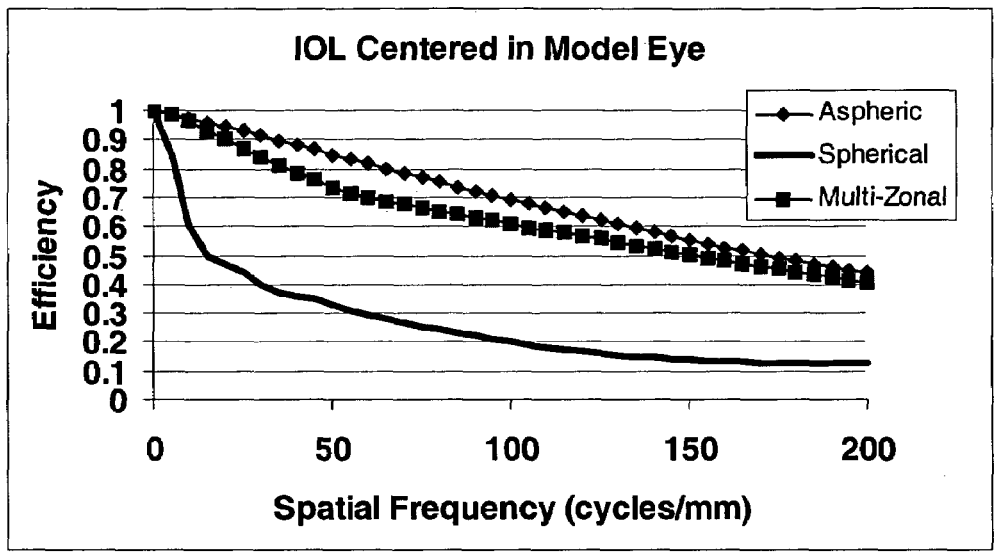
FIGS. 6A and 6B show simulated modulation transfer functions for an aspheric, spherical and multi-zonal monofocal IOLs at a 5 mm pupil diameter with no decentration and 0.5 mm decentration, respectively.
Figure 6B:
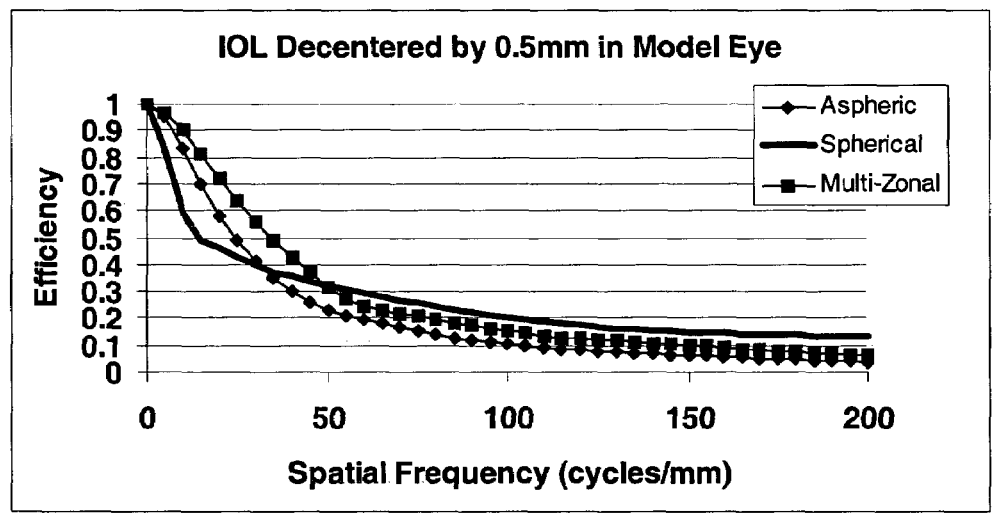

Notes:
1. IOL refractive index at 35° is 1.47;
2. IOL central thickness is 0.977 mm.
3. IOL nominal base power = 20D FIGS. 6A and 6B illustrate the IOL performance the multi-zonal monofocal lens shown in Table 1 in terms of the simulated modulation transfer functions as compared to both a spherical lens and an aspheric lens (the TECNIS brand of lens). These simulated results are based on a 5 mm pupil diameter with no decentration (FIG. 6A) and 0.5 mm decentration (FIG. 6B). FIG. 6A illustrates the performance for each type of lens when the lenses are precisely centered within the eye. In FIG. 6B, the performance of each type of lens is illustrated when the lens is decentered from the optical axis of the eye by 0.5 mm, a condition that is not uncommon under realistic conditions.

In comparing FIG. 6B to FIG. 6A, it can be seen that with decentration, both the aspheric and multi-zonal monofocal designs suffer a large loss in image quality (e.g., MTF). However, the multi-zonal loss is less compared to the aspheric design. Observe in FIG. 6A that the aspheric and multi-zonal MTFs are significantly higher compared to the standard spherical surface design. The price paid for the significant enhancement of image quality is the sensitivity to non-nominal conditions (e.g., decentration) shown in FIG. 6B. However, some improvement in the non-nominal condition can be achieved by this novel use of zones in the design of an improved monofocal IOL. The price paid for the reduction in non-nominal sensitivity is the slightly lower multi-zonal design MTF compared to the aspheric MTF shown in FIG. 6A. Never-the-less, the multi-zonal MTF remains significantly improved compared to the spherical design MTF.

Figure 7:
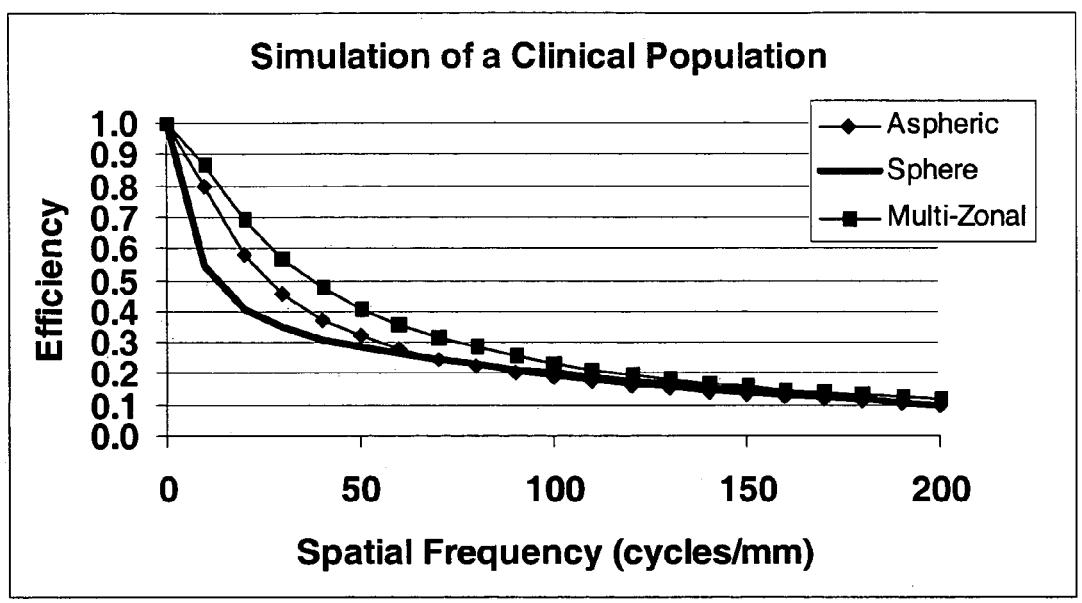
FIG. 7 show simulated aspheric, spherical, and multi-zonal monofocal IOL MTF curves at a 5 mm pupil diameter representing the respective average MTFs over 100 eyes varying in corneal aberrations, IOL decentration and tilt, and small pupil size changes.

FIG. 7 illustrates the results of a Monte Carlo simulation in the form of plots of the average MTF performance for spherical, aspheric, and multi-zonal monofocal IOLs based on over 100 different eyes and under varying conditions of corneal aberrations, IOL decentration, and IOL tilt. The simulation was conducted using a 5 mm nominal pupil diameter. The results compare the average performance of the various types of lenses under simulated, real-world conditions.

In clinical practice, many non-nominal conditions exist. These include corneas with different aberrations, different amounts of IOL tilt and decentration, and different pupil sizes for a nominal lighting condition. Other conditions may apply in more unique circumstances. Randomly selected values of the above "conditions" were selected, individual MTFs calculated, and the average MTF tabulated. In effect, this procedure simulates the general clinical population and assesses the complex interaction of the IOL surface design and aberrations induced by the non-nominal conditions.

FIG. 7 shows the results of such a "clinical simulation", comparing the aspheric, spherical, and multi-zonal designs. FIG. 7 suggests that the aspheric design will improve the MTF at lower spatial frequencies compared to the spherical design. From the patient's perspective, objects will have a higher contrast and color will appear richer. FIG. 7 predicts that the multi-zonal design will provide even more improvement over a wide range of spatial frequencies. The patient should experience both improved contrast and visual acuity. The latter is related to changes in MTF at about 100 cycles/mm. As expected, when averaged over an entire clinical population, the multi-zonal design provides more improvement compared to an aspheric design, even though the multi-zonal design is slightly lower in performance in the nominal condition (FIG. 6a).

In certain embodiments, a method of designing a multi-zonal monofocal IOL comprises providing an optical model of the human eye. The model may include a corona, an iris, the IOL 60, a retina, and any liquids, substances, or additional devices between the these components. The model may also include various system design parameters such as the spacing between components and refractive index values.

The method further comprises providing an optical model of a lens comprising an inner zone, an intermediate zone, an outer zone, and zonal design parameters (e.g., the IOL 60). The zonal design parameters for each of the zones may include, but are not limited to, a radius of curvature, surface polynomial coefficients, inner radius, outer radius, refractive index, and DOE characteristics. In certain embodiments, the model may include additional zones along with their corresponding parameters. One of the zonal design parameter may also include the number of zones in the lens. The model may comprise the zones and zonal design parameters for an anterior surface of the lens, the posterior surface of the lens, or both surfaces of the lens.

The method further comprises adjusting the zonal design parameters based on an image output parameter for one or more non-optimal states of the lens. Examples of non-optimal states include, but are not limited to, IOL decentration and tilt, and different corneal aberrations (e.g., different corneal asphericities). Examples of image output parameter include, but are not limited to, the Modulation Transfer Function, spot radius, and/or wavefront error. Alternatively, a plurality of output parameters may be used for evaluation while adjusting the zonal design parameters.

With the IOL in a non-optimal state, zonal design parameters such as the number of zones and zone radii may be adjusted to correct any aberrant light rays entering the system entrance pupil. For example, in the case of IOL decentration and a three-zone lens, the first zone radius and second zone radius are chosen such that the second zone falls within the entrance pupil. The zonal design parameters for the zones exposed by light entering the system entrance pupil may be adjusted to compensate for the aberrations produced by the non-optimal state. Preferably, the zonal design parameters are adjusted until the image output parameter obtains an optimized or threshold value.

The method may also include adjusting the zonal design parameters and/or the other system design parameters of the optical model based on the image output parameter for an optimal state of the lens. Such an optimal state would preferably represent a condition in which the IOL is centered along the optic axis of the eye and normal thereto.

The method may be realized using optical design software that is resides on a computer or other processing device. The optical design software may be used to numerically ray-traces various sets of light rays through optical model and that evaluates the image formed on the retina. Recognizing that the modeled cornea has finite aberrations, the design parameters of the multi-zonal monofocal IOL may be adjusted to improve the quality of the image formed on the retina in terms of the image output parameter or in terms of a plurality of image output parameters.

The resulting lens from this design may produce slightly lower retinal image quality when placed in the optimal state as compared to the optimal design in the optimal state. However, such a non-optimal state design will still allow a lens to be produced that provides significantly better performance than that possible using spherical optics. Thus, the non-optimal state design provides superior performance over a greater range of non-optimal conditions as compared to the initial optimal-design.

In certain embodiments, additional non-optimal states are used to further adjust the design parameters in order to provide a design that is suitable of a particular condition or set of conditions. The results using various non-optimal states may be used to provide a lens suited for a plurality of anticipated non-optimal states of an IOL within an eye or certain population of eyes having certain aberrations. For instance, the method may be used for testing the lens over a plurality of corneal surface variations and dispositions of optical elements in the eye's optical system using tolerance analyzing techniques. Additionally, all or part of the method may be repeated one or more times to modify zonal parameters and achieve a better average optical performance. Known algorithms, such as assigning weighting functions to the various non-optimal states, may be used to provide a lens with desired characteristics.

While embodiments of the invention have been disclosed for an IOL suitable providing enhanced performance under non-optimal conditions, such as when the IOL is decentered from the optical axis of the eye, those skilled in the art will appreciate that embodiments of the invention are suitable for other ocular devices such as contact lenses and corneal implants. For instance, the method of designing a multi-zonal monofocal IOL may be adapted for improving the performance of contact lenses, which are known to move to different positions during use relative to the optical axis of the eye.

While this invention has been described with respect to various specific examples and embodiments, it is to be understood that these are merely exemplary and that the invention is not limited thereto and that it can be variously practiced within the scope of the following claims.

What is claimed is:

1. A multi-zonal monofocal ophthalmic lens comprising:
    an optic comprising a plurality of zones, including:
        an inner zone having a first optical power;
        an intermediate zone surrounding the inner zone and having a second optical power that is different from the first power by a magnitude that is less than about 0.75 Diopter; and
        an outer zone surrounding the intermediate zone having a third optical power different from the second optical power;
    the plurality of zones all disposed such that light entering the entire optic from a distant point source is focused to substantially a single point;
    wherein the third optical power is equal to the first optical power.

2. A method of designing a multi-zonal monofocal ophthalmic lens, comprising:
    providing an optical model of the human eye;
    providing an optical model of a lens comprising an inner zone, an intermediate zone, an outer zone, and zonal design parameters, the inner zone, the intermediate zone, and the outer zone disposed such that all light entering the inner zone, the intermediate zone, and the outer zone of the monofocal ophthalmic lens from a distant point source is focused to substantially a single point;
    adjusting the zonal design parameters based on an image output parameter for one or more non-optimal states of the lens; and
    testing the intraocular lens over a plurality of corneal surface variations and dispositions of optical elements in the eye's optical system using tolerance analyzing techniques.

3. A method of designing a multi-zonal monofocal ophthalmic lens, comprising:
    providing an optical model of the human eye;
    providing an optical model of a lens comprising an inner zone, an intermediate zone, an outer zone, and zonal design parameters, the inner zone, the intermediate zone, and the outer zone disposed such that all light entering the inner zone, the intermediate zone, and the outer zone of the monofocal ophthalmic lens from a distant point source is focused to substantially a single point;
    adjusting the zonal design parameters based on an image output parameter for one or more non-optimal states of the lens; and
    repeating at least a portion of the method to modify zonal parameters and achieve a better average optical performance.

* * * * *